April 12, 1966 R. L. SUMRULD Plant Pat. 2,619
PLUM TREE
Filed Dec. 21, 1964
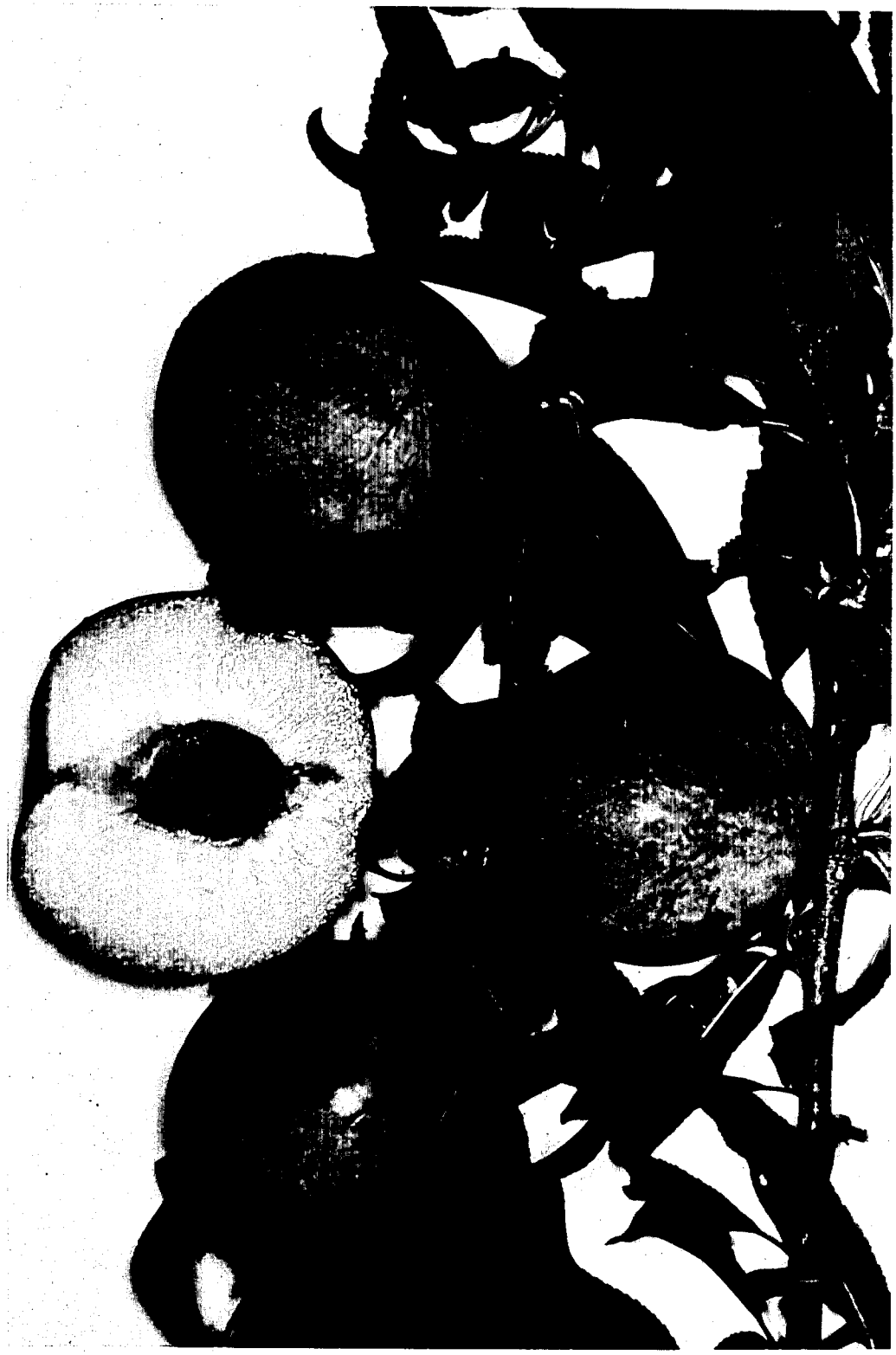
ROY L. SUMRULD
INVENTOR
Haubner & Worrel
ATTORNEYS United States Patent Office Plant Pat. 2,619
Patented Apr. 12, 1966

2,619
PLUM TREE

Roy L. Sumruld, 2957 E. Tulare St., Tulare, Calif.

Filed Dec. 21, 1964, Ser. No. 420,234
1 Claim. (Cl. Plt.—38)

The present invention relates to a plum tree and more particularly to a new and distinct variety thereof broadly characterized by regular bearing of high quality fruit for commercial shipping, the vigorous growth of the tree, and the extremely late ripening period of the fruit, which occurs as long as two months after the ripening of fruit of other commercially grown plum trees, such as the late Santa Rosa (unpatented).

In the commercial growing of fruit trees, it is economically advantageous to be able to market fruit at a time other than during the period when the bulk of the same generic fruit is produced. This is particularly true in the case of fruit having characteristics adapting it for shipment to markets outside the local production area. In the case of the present invention, the fruit of trees of the new variety ripens as late as two months after the late Santa Rosa (unpatented) plum tree and as late as one month after the Casselman (unpatented) plum tree, which is a mutation of the late Santa Rosa. Therefore, this new plum variety satisfies a primary object of producing a late ripening, high quality fruit, which has a firm flesh of delicate, somewhat acid flavor and capable of withstanding shipment over long distances, while maintaining its appearance and eating quality.

I discovered the present variety of plum tree on my farm near Tulare, California, located in the San Joaquin Valley. During the year 1958, I observed a sport limb growing from a late Santa Rosa (unpatented) plum tree planted on my farm. The sport limb was noted and observed throughout the subsequent season. The principal distinguishing characteristic was the fact that fruit ripened on the sport about two months later than that of trees of the late Santa Rosa variety. For example, ripened fruit was picked from the sport on or about October 5, 1959.

During the year 1960, I grafted nine trees from cuttings taken from the sport limb first observed in 1958. These nine trees each exhibited the characteristics of the sport limb, and bore fruit in 1964 ripening during a period approximately two months later than the aforesaid late Santa Rosa (unpatented) variety. During 1964, fruit was first picked from these nine trees on September 25, and the date of the last picking was October 20, 1964.

The accompanying drawing is a color photograph of a characteristic twig of the subject plum tree bearing foliage and a mature fruit, and also shows a fruit of the new variety divided on its suture plane to reveal flesh coloration and pit characteristics.

Referring more specifically to the pomological details of this new and distinct variety of plum tree, the following has been observed under the climatic conditions prevailing at my farm near Tulare, California, and is an outline description thereof. All major color plate identifications are by reference to Maerz and Paul Dictionary of Color.

*Tree*

Size: Large, vigorous, upright, vase formed by pruning, productive, and regular bearer.

Trunk: Medium-slender, shaggy, brownish-grey. Lenticels—numerous, medium.

Leaves (selected from midportion of vigorous unbranched terminal shoots):

*Length.*—Average about 4–5".

*Width.*—Average about 1½–2".

*Form.*—Medium, obovate, tip acuminate, medium-thick.

*Color.*—Dark green (22–L–8).

*Vein color.*—Light green (20–E–1).

*Margin.*—Glandular-crenate.

*Petiole.*—Medium in length, medium-slender in thickness.

*Deciduous.*—Held leaves late like late Santa Rosa.

*Glands.*—None on most—1–3 on largest leaves. Average number 1–3, alternate, small, reniform, green (dark green to dark brown), position—petiole and base of leaf.

*Fruit*

Maturity when described: Firm ripe, date October 13, 1964.

Size: Variable, large, medium. Diameter—axial 2–2½", average 2¼". Transverse in suture plane—1¾–2¼", average 2". At right angles to suture plane—2–2½", average 2¼".

Form: Variable, oblong.

Suture: Distinct but shallow. Extends from base to beyond. Has slight depression beyond pistil point.

Ventral surface: Rounded, no lips.

Cavity: Medium flaring and shallow. Slightly elongated in suture plane. Depth—⅛–¼". Breadth—5/16–½". No markings.

Base: Retuse.

Apex: Retuse. Pistil point.—apical.

Stem:

*Length.*—⅜–½".

*Diameter.*—1/16"—about.

*Adherence to stone.*—Infrequent.

Skin: Thick-medium. Medium-tender. Tenacious to flesh.

*Tendency to crack.*—Very slight. Some cracking along suture at stem end on a few.

*Color.*—Red-blue (2–B–11 to 6–L–6), mottled greenish yellow background, or undercolor (11–L–1), to orange-yellow (9–L–4). Has small irregular dark stripe along suture on most fruit (7–C–5).

*Down.*—None.

Flesh:

*Color.*—Uniform light yellow (9–K–2), when freshly cut.

*Surface of pit cavity.*—Slightly dark yellow (10–K–5).

*Juice.*—Abundant.

*Texture.*—Firm, meaty.

*Fibers.*—Few.

*Ripens.*—Evenly.

*Flavor.*—Subacid, mild, delicate.

*Eating quality.*—Good.

Stone: Free.

*Adheres to flesh.*—Infrequently, only along suture edge. Pulls away from the stems leaving a cavity about ¼–½" in diameter and irregular in shape.

*Fibers.*—Short.

*Free.*—Retains short fiber-like threads along suture ridges.

*Size.*—Length—⅞–1⅛", average 1". Breadth—9/16–¾", average ⅝". Thickness—average ⅜".

*Form.*—Obovate, some oval; tip acuminate.

*Base.*—Usually straight.

*Hilum.*—Oval.

*Apex.*—Acuminate.

*Sides.*—Usually equal. Few flattened on one side.

*Surface.*—Fairly smooth, slightly furrowed near base.

*Ventral edge.*—Thick, with usually one groove.

*Dorsal edge.*—Usually with one groove, some with none or very small groove.

*Color of stone.*—When fresh from the fruit and moist (11–U–8) with dark area at stem (15–A–12).

*Tendency to split.*—Slight when dry.

Use: Market, local, dessert, culinary and long distance shipping.

Keeping Quality: Good.

Shipping Quality: Good.

Although the new variety of plum tree possesses the described characteristics under the growing conditions in Tulare County, California, having been first observed near Tulare, Tulare County, California, at the southern end of the San Joaquin Valley, it is to be understood that variation of the usual magnitude in characteristics incident to the growing conditions, fertilization, pruning and pest control are to be expected.

Having thus described and illustrated my new variety of plum tree, what is claimed as new and desired to be secured by Letters Patent is:

A new and distinct variety of plum tree substantially as illustrated and described and which is characterized by its vigorous growth, its bark being somewhat smoother than the late Santa Rosa (unpatented) plum tree, which it most nearly resembles, but from which it is distinguished by its regular bearing of medium-large, freestone, yellow-fleshed fruit of firm, meaty texture of mild subacid flavor, and its ripening at about two months later than the fruit of the late Santa Rosa plum tree and about one month later than that of the Casselman (unpatented) plum tree.

No references cited.

ABRAHAM G. STONE, *Primary Examiner.*